United States Patent [19]

Tamm

[11] Patent Number: 4,953,977
[45] Date of Patent: Sep. 4, 1990

[54] ELECTROTHERMAL ATOMIZATION FURNACE

[75] Inventor: Rolf Tamm, Salem, Fed. Rep. of Germany

[73] Assignee: Bodenseewerk Perkin-Elmer & Co., GmbH, Überlingen, Fed. Rep. of Germany

[21] Appl. No.: 285,884

[22] Filed: Dec. 16, 1988

[30] Foreign Application Priority Data

Dec. 19, 1987 [DE] Fed. Rep. of Germany ....... 3743286

[51] Int. Cl.⁵ ............................................. G01N 21/74
[52] U.S. Cl. .................................... 356/312; 356/244
[58] Field of Search ................................. 356/312, 244

[56] References Cited

U.S. PATENT DOCUMENTS

| 3,778,156 | 12/1973 | Schmedes et al. | 356/244 |
| 3,817,629 | 6/1974 | Witte | 356/244 |
| 3,819,279 | 6/1974 | Braun | 356/244 |
| 4,098,554 | 7/1978 | Huber et al. | 356/312 |
| 4,111,563 | 9/1978 | Tamm | 356/244 |
| 4,303,339 | 12/1981 | Glaser et al. | 356/244 |
| 4,407,582 | 10/1983 | woodriff | 356/312 |

FOREIGN PATENT DOCUMENTS

| 2225421 | 12/1973 | Fed. Rep. of Germany . |
| 3534417 | 4/1987 | Fed. Rep. of Germany . |
| 3545635 | 6/1987 | Fed. Rep. of Germany . |
| 0097040 | 6/1984 | Japan ..................... 356/312 |
| 126232 | 7/1984 | Japan ..................... 356/312 |

OTHER PUBLICATIONS

Falk et al, *Fresenius Z. Anal Chem.* 323, 1986, pp. 748-753.
Patents Abstracts of Japan, Sect. p, vol. 8, Sep. 29, 1984, No. 214, (P-304).

*Primary Examiner*—F. L. Evans
*Attorney, Agent, or Firm*—Edwin T. Grimes; Thomas P. Murphy

[57] ABSTRACT

A furnace for electrothermal atomization of samples for atomic absorption spectroscopy comprises a tubular furnace body with lateral inlet aperture and sample-holding inner body which has a hollow, generally semi-cylindrical shape. The inner body is located within the furnace body opposite the inlet aperture and is connected to the furnace body by a single web. In one embodiment the web is provided with axial bores and the inner surface of the sample holder has a plurality of projections forming a portion of a screw thread. In another embodiment, two hollow, generally semicylindrical bodies extend around the furnace body and thereby define a cavity and a slot. The furnace body and two hollow, generally semicylindrical bodies are interconnected by lateral webs. Electrical contacts members are provided on the semicylindrical bodies. The entire furnace is one integral graphite element.

19 Claims, 3 Drawing Sheets

ELECTROTHERMAL ATOMIZATION FURNACE

BACKGROUND AND SUMMARY OF THE INVENTION

The present invention relates generally to atomic absorption spectroscopy and more particularly to a furnace for electrothermal atomization of samples in atomic absorption spectroscopy.

Atomic absorption spectroscopy is an analytical method for determining the amount or concentration of a looked-for element in a sample. The sample is atomized such that its elements are present in atomic state in a "cloud of atoms". A measuring light beam from a line emitting light source which comprises the resonant spectral lines of the looked-for element is passed through this cloud of atoms. The concentration of the looked-for element in the sample can be determined from the attenuation of the measuring light beam in the cloud of atoms after calibration with a known sample.

Electrothermal atomization of the sample is preferable for high sensitivity measurements. In electrothermal atomization, the atomization of the sample and the generation of the cloud of atoms takes place in a electrically heated furnace. Generally, this furnace is a suitably designed graphite body referred to as a graphite tube atomizer which is heated by a high electric current. The sample is introduced into this furnace which is heated to high temperature by passing electrical current therethrough. The sample is thereby first dried, then ashed and lastly atomized. A "cloud of atoms" is accordingly generated in the furnace which contains the looked-for element in an atomic state. The measuring light beam is passed through this furnace.

Generally, these furnaces consist of a small tube made of graphite which is held between two annular contacts. A high electrical current is passed through the contacts and through the tube in its longitudinal direction. Thus, the tube can be heated to high temperatures. In operation, the sample is inserted into the tube through a lateral inlet port and is atomized when the tube is heated up. The measuring light beam passes through the annular contacts and longitudinally through the bore of the tube in its longitudinal direction. The graphite tube is surrounded by an inert gas on the inside and outside which prevents the tube from contacting air oxygen. Such graphite tube atomizers are illustrated and described in the commonly owned Schmedes et al., U.S. Pat. No. 3,778,156 issued Dec. 11, 1973 and Huber et al., U.S. Pat. No. 4,098,554 issued July 4, 1978 (both incorporated herein by reference).

In the commonly owned R. Tamm, U.S. Pat. No. 4,111,563 issued Sept. 5, 1978 (which is incorporated herein by reference), a graphite tube is shown in which a tubular inner body member is arranged in the central area within the tubular furnace body which is open at both ends with the tubular inner body member being substantially shorter than the furnace body. The inner body is arranged concentric in the furnace body and extends only through the central area of the furnace body. A lateral inlet port is centrally positioned in the furnace body in alignment with an inlet port in the tubular inner body. The inner body is connected with the furnace body through longitudinally extending webs which extend in the longitudinal plane perpendicular to the inlet port.

The furnace of Tamm reduces errors in measurement due to unhindered spreading of the liquid sample over the inner wall of the graphite tube. If the liquid reaches the relatively cool end portions of the tubular furnace, there may only be an incomplete vaporization such that sample material is retained in the furnace which will disturb subsequent measurements of other samples. Further, this configuration inhibits the infiltration of the liquid sample into the inner wall and avoids sample losses which can occur by the seeping of sample liquid into the porous graphite.

It is desirable to delay the atomization of the sample relative to the heating of the furnace wall. An adequate atomization delay ensures that the components of the atomized sample do not precipitate on relatively cool wall portions and that the sample is atomized as abruptly as possible to generate a strong absorption signal. From L'vov's publication in "Spectrochimica Acta" vol. 338, 153–193 a generally rectangular platform, made of pyrolytic graphite, is known which is inserted into a furnace designed as a graphite, tube. In order to reduce the contact with the graphite tube wall, cutouts are provided along the longitudinal edge of the platform. As a result, the sample is heated substantially indirectly by radiation of the inner wall of the furnace.

In the commonly owned Glaser et al., U.S. Pat. No. 4,303,339 issued Dec. 1, 1981 (which is incorporated herein by reference), an inner body in the shape of a platform is shown which has a recess for accommodating the sample and which is guided at the outer body only along two opposite longitudinal edges. The amount of sample which can be accommodated by this platform is limited. The handling of the platform is complicated and requires considerable skill, i.e., into a small furnace body, an even smaller platform has to be inserted which is a very complicated manipulation. Furthermore, some electrical current flowing through the furnace body in the longitudinal direction is also flowing through the platform so as to generate heat. Therefore, the platform is not only heated indirectly by radiation but also by Joul's heat generated in the platform itself.

It is a object of the present invention to provide a new and improved furnace for electrothermal atomization.

Another object of the invention is to provide such a furnace which avoids sample precipitation or collection on the interior furnace wall.

A further object of the invention is to provide such a furnace wherein the sample is heated indirectly on a platform with a predetermined delay relative to the heating of the furnace body.

Another object of the invention is to provide such a furnace wherein a sample held on a sample platform is predominantly heated by heat radiation from the furnace wall.

Another object of the invention is to provide such a furnace which avoids difficult handling and positioning of a platform and insures the platform is exactly positioned in the furnace body.

Yet another object of the invention is to provide such a furnace which is economical to manufacture.

Other objects will be in part obvious and in part pointed out more in detail hereinafter.

Accordingly, it has been found that the foregoing and related objects are attained in an electrothermal atomization furnace having a tubular electrothermal furnace body with an integral sample platform. The sample platform is hollow, generally semicylindrical shape and is integrally connected to the furnace body by a web configured and positioned to sufficiently impede heat conduction from the furnace body to the platform so that sample on the platform is thermally atomized substantially by radiation from the furnace body.

The inner body is integral with the tubular outer furnace body and therefore the furnace with the inner body can be handled easily. In contrast to U.S. Pat. No. 4,111,563, however, the inner body is not a closed tube but is a hollow, generally cylindrical shape and is open to the inner wall of the furnace body. Therefore, the sample supplied to the inner body is heated with a delay relative to the furnace body. Although the inner body in U.S. Pat. No. 4,111,563 is also heated with delay relative to the actual furnace body, the sample does not "see" the inner wall of the furnace body but rather the sample sees the inner wall of the inner body and is heated together with this inner body. Therefore, the effect which should be achieved by delayed heating of the sample does not occur in the arrangment described in U.S. Pat. No. 4,111,563. On the contrary, the same undesirable effects—now with respect to the inner body—occur which should be avoided by the platforms according to L'vov's publication and according to U.S. Pat. No. 4,303,339. In the present invention, the furnace is easily handled. The hollow, generally semicylindrical design of the inner body offers the advantage that larger amounts of sample can be dosed. The present furnace is economical to manufacture because manufacturing includes lathing, boring, and milling processes which are easily carried out.

DESCRIPTION OF THE PREFERRED EMBODIMENT

Figure 1:
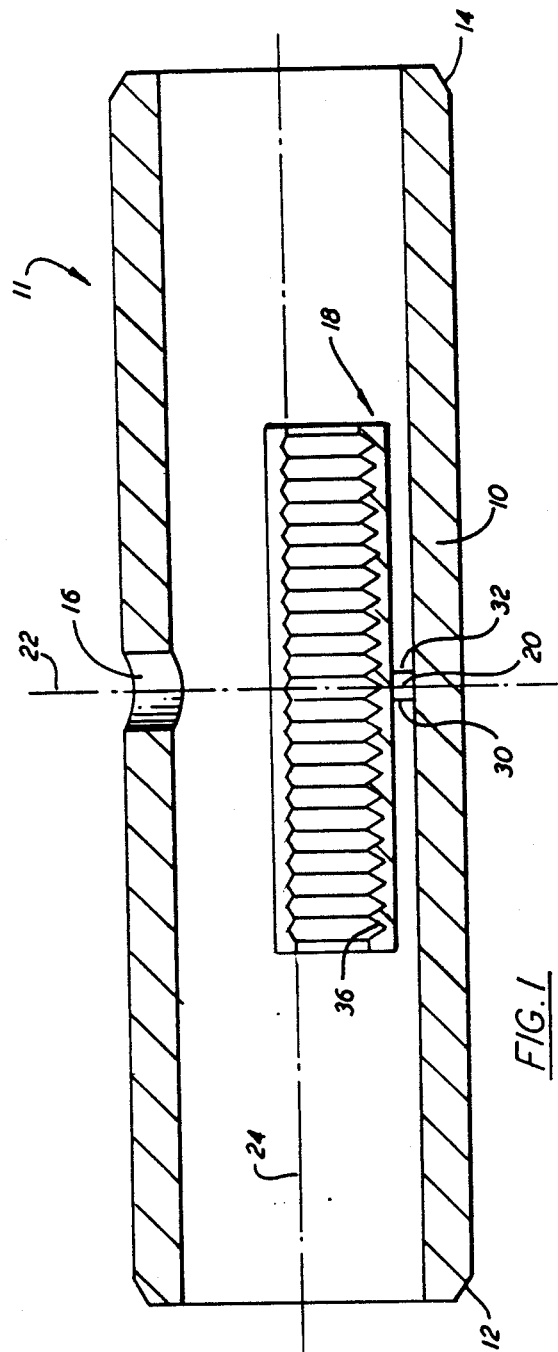
FIG. 1 Is a longitudinal sectional view of an electrothermal atomization furnace according to the present invention.

Although specific forms of the present invention have been selected for illustration in the drawings, and the following description is drawn in specific terms for the purpose of describing these forms of the invention, the description is not intended to limit the scope of the invention which is defined in the appended claims.

Referring to FIG. 1, the electrothermal furnace of the present invention is generally designated by the numeral 11. The numeral 10 designates a tubular outer furnace body made of graphite and having a pair of contact surfaces 12, 14 and a lateral inlet port 16. The conical contact surfaces 12 and 14 are provided at the end faces of the furnace body 10 to cooperate with corresponding surfaces of annular contacts on the side of the spectroscopic instrument (not illustrated). The furnace body 10 is mounted and held between these corresponding surfaces. Through these contacts on the side of the instrument a current is passed longitudinally through the furnace body 10 to heat the furnace body 10. The lateral inlet port 16 is positioned in the center of the furnace body 10.

The outer furnace body 10 is integral with an inner body 18 having a hollow, generally cylindrical shape. The inner body 18 extends in a circumferential direction through about 180° and in the longitudinal direction through the central area of the furnace body 10. The inner body 18 is positioned opposite the inlet port 16 and is substantially shorter than the furnace body 10.

Figure 2:
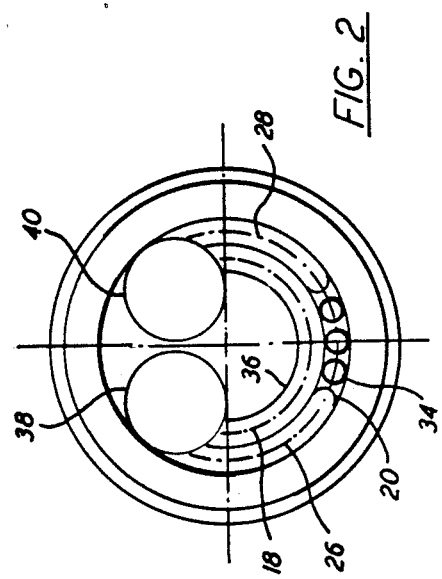
FIG. 2 Is an end view of the furnace of FIG. 1

A web 20 connects the inner body 18 to the outer furnace body 10. The web 20 is arranged symetrically to the center plane determined by the axis of the inlet port 16 and the longitudinal axis 24 of the furnace body 10 and opposite the inlet port. This center plane is the plane of the paper in FIG. 1. As shown in FIG. 2, the web 20 extends through a substantially smaller angle compared to the generally semicylindrical inner body 18 and symetrical to the longitudinal center plane. In this way, arcuate recesses 26 and 28 are formed in the area of the web 20 between the inner wall of the furnace body 10 and the outer wall of the inner body 18.

The web 20 is longitudinally limited by the planar surfaces 30 and 32 and is symmetrical to a radial plane comprising the axis 22 of the inlet port 16. A plurality of axial bores 34 extend through the web 20.

In this furnace configuration, no current flows through the inner body 18 as the different points of the web 20 have substantially the same potential. Therefore, there is no direct heating of the inner body by Joul's heat. Furthermore, the web 20 is narrow and its cross-section is further reduced by the bores 34. Therefore, the local heating by heat conduction is also kept small. A sufficient mechanical stability is also maintained.

The sample supplied to the inner body 18 through the inlet port 16 is heated as the inner body 18 itself, i.e., substantially indirectly by the radiation of the hot inner wall of the furnace body 10. This ensures that the sample is only atomized when the furnace body 10 has reached the atomization temperature so as to prevent deleterious sample precipitation. It is the outer furnace body 10 at which atomized sample atoms would precipitate if portions thereof have not reached the atomization temperature.

The inner wall of the hollow, generally semicylindrical inner body 18 is provided with a plurality of projections 36 which form part of a screw thread. The projections 36 ensure that the inner body accommodates a larger amount of sample and also counteract distribution of the sample along the inner body 18.

The manufacture of the furnace 11 is relatively easy and economical. Specifically, the tubular furnace body having a concentric, tubular inner body which is connected at its center to the furnace body through an annular web is made by lathing. Then, the tubular inner body is threaded. Approximately half of the inner body is removed to form the hollow, generally semicylindrical inner body 18 by two bores, indicated in FIG. 2 and designated by the numerals 38 and numeral 40. The bores 34 in the web 20 are made. The recesses 26 and 28 are milled and, finally, the inlet port 16 is bored.

Accordingly, the atomization furnace described ensures that a furnace can be made of graphite as one integral part and having a platform opposite the inlet port. The entire arrangement is mechanically stable and shows favorable characteristics with respect to the atomization process as well as with respect to the sample accommodated.

Figure 3:
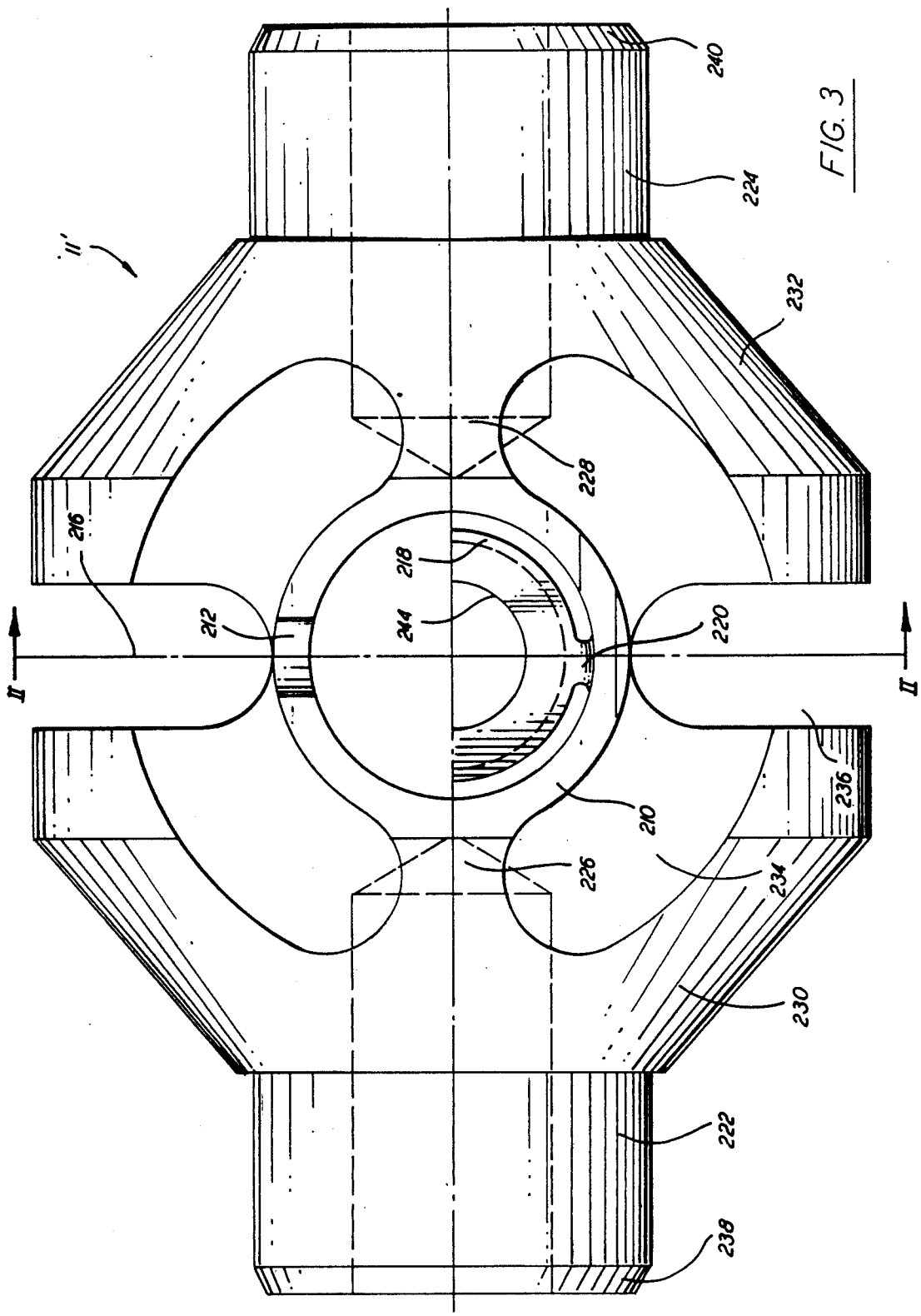
FIG. 3 Is a schematic view in the direction of the axis of the tubular furnace body of an alternate embodiment of the present invention.
Figure 4:
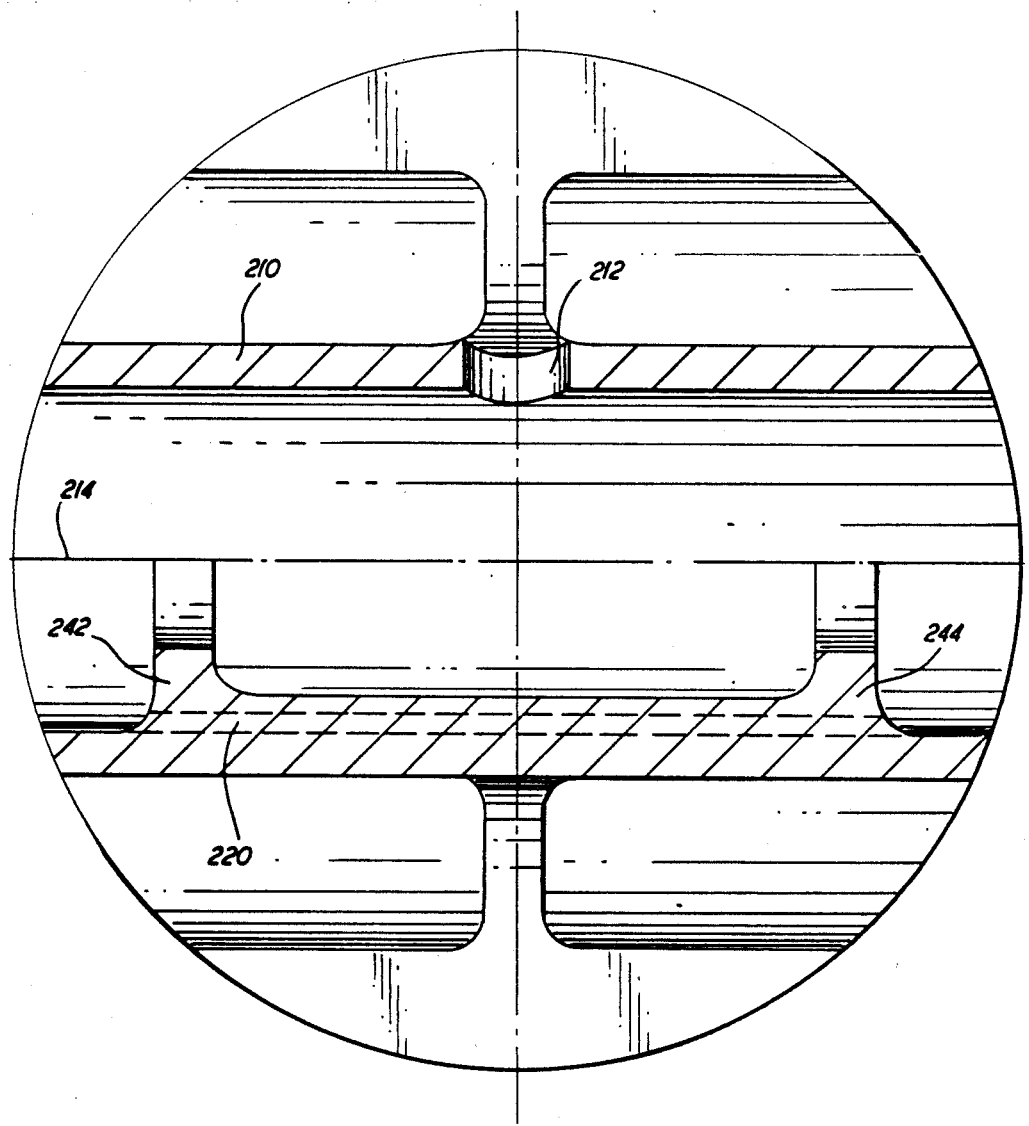
FIG. 4 Is a longitudinal sectional view taken along line IV—IV of FIG. 3.

Referring to the further embodiment of FIGS. 3 and 4, the electrothermal furnace 11' comprises a tubular, electrically-conductive furnace body 210 made of graphite with an integral inner body or platform 218. The furnace body 210 has a lateral or radial inlet aperture 212 positioned in the central area of the furnace body 210 as seen in FIG. 4. A longitudinal center plane 216 of the furnace is defined by the axis of the inlet aperture 212 and the axis 214 of the furnace body 210. The section view of FIG. 4 is taken along the longitudinal center plane 216.

The inner body 218 is positioned within the tubular furnace body 210 and is integral therewith. The inner body 218 is configured to extend only over the central area of the furnace body 210.

The inner body 218 has a hollow, generally semicylindrical shape and, as shown in FIG. 3, it forms a hollow semicylinder extending over 180° about its axis. The inner body 218 is arranged symmetrical with respect to the longitudinal center plane 216 opposite of the inlet aperture 212. In use, the inlet aperture 212 is disposed upwardly as seen in FIG. 3 and the longitudinal center plane 216 extends vertically. The inner body 218 is located within the furnace body at the bottom thereof below the inlet aperture 212 and is connected to the tubular furnace body 210 by one single web 220. The web 220 is configured to sufficiently impede heat conduction from the furnace body 210 to the inner body 212 so that a sample on the inner body 218 is thermally atomized substantially by radiation from the furnace body. The web 220 is arranged in the longitudinal center plane 216 of the furnace and on the side opposite the inlet aperture 212. The inner body 218 has upwardly projecting collars 242, 244 at its opposite ends as shown in FIG. 4 to form a trough-shaped platform for safely retaining liquid sample thereon.

The furnace body 210 is electrically heated through contacts 222 and 224 arranged laterally on the furnace body 210 such that electrical current will flow in the circumferential direction of the tubular furnace body 210. Consequently, all locations of the web 220 have substantially the same potential so that current does not flow through the inner body 218. Therefore, the inner body 218 is not directly heated by electric current.

Two hollow, generally semicylindrical bodies 230 and 232 are interconnected to furnace body 210 by webs 226 and 228 respectively which extend perpendicular to the longitudinal center plane 216. The semicylindrical bodies 230 and 232 extend around the furnace body 210 on both sides such that a cavity 234 is formed which surrounds the furnace body 210. A slot 236 is formed between the semicylindrical bodies 230 and 232 which is symmetrical with respect to the bodies 230, 232 and includes the longitudinal center plane 216. The inlet aperture 212 of the furnace body 210 is accessible through the slot 236.

The cylindrical contacts 222 and 224 are integral with the bodies 230 and 232, respectively, and arranged so that their axes extend perpendicular to the longitudinal center plane 216. Thus, the contacts 222, 224 are in electroconductive connection only through the furnace body 210. The contacts 222, 224 form conical contact surfaces 238 and 240 at their ends for mounting the furnace between electrodes (not shown) on the sides of the apparatus. Inert gas can be introduced into the cavity 234 through the contacts in a conventional way which need not be illustrated in detail.

As shown in FIG. 3, the webs 226 and 228 are constricted so as to have a higher electric resistance. As a result, increased Joul's heat and a higher temperature is generated in the webs. Consequently, heat dissipation from the hot furnace body 210 to the relatively cold contacts 222 and 224 is impeded and equal temperature distribution in the furnace body 210 is ensured.

As can be seen, an integral graphite atomizer furnace has been provided which avoids sample precipitation or collection on the interior furnace wall and which atomizers the sample predominantly by heat radiation from the furnace wall. The sample is heated indirectly on the platform with a desired delay relative to the heating of the furnace body. Moreover, the position of the platform is fixed so that manipulation of the platform is avoided and the measuring light beam is not unduly constricted.

As will be apparent to persons skilled in the art, various modifications and adaptations of the structure above described will become readily apparent without departure from the spirit and scope of the invention, the scope of which is defined in the appended claims.

What is claimed is:

1. An electrothermal atomization furnace comprising:
a tubular electrothermal furnace body adapted for passing a radiation beam therethrough, said furnace body having a centrally positioned lateral inlet aperture,
means for passing an electrical current through said furnace body to heat said furnace body sufficient to atomize a sample on a platform within said furnace body,
an elongated sample platform having a sample holding recess and being positioned centrally within said furnace body opposite said inlet aperture and integrally connected to said furnace body,
web means for integrally connecting said platform to said furnace body, said web means being configured and positioned to maintain a substantially uniform electrical potential thereacross to substantially prevent a heat-generating current flow through said platform when current flows through said furnace body and to sufficiently impede heat conduction from said furnace body to said platform so that sample on said platform is thermally atomized substantially by radiation from said furnace body,
said furnace body having a longitudinally axis and a longitudinal center plane containing said axis and extending through said inlet aperture,
said web means comprising a single web extending between said furnace body and said platform and positioned in said center plane,
said platform having a hollow, generally semicylindrical shape and disposed between said inlet aperture and said web and symmetrically arranged relative to said center plane,
said means for passing an electrical current comprising first and second electrical contacts disposed laterally on said furnace body so that electrical current flows in a circumferential direction through said furnace body and said web being positioned so that all points on said web have substantially the same electrical potential,
first and second generally semicylindrical hollow body members being oppositely disposed and extending around said furnace body to form a slot therebetween with said center plane extending through said slot, said first body member having a first web portion extending perpendicular to said center plane and connecting said first body member to said furnace body, said second body member having a second web portion extending perpendicular to said center plane and connecting said second body member to said furnace body said first contact being integral with said first body member and having a longitudinal axis extending perpendicular to said center plane, and said second contact being integral with said second body member and having a longitudinal axis extending perpendicular to said center plane.

2. The device of claim 1 wherein said first and second web portions are constricted to increase electrical resistance and impede heat conduction therethrough.

3. The device of claim 1 wherein said first and second contacts each have a conical distal end adapted for mounting the furnace between electrodes.

4. An electrothermal atomization furnace comprising:

a tubular electrothermal furnace body adapted for passing a radiation beam therethrough, said furnace body having a centrally positioned lateral inlet aperture, means for passing an electrical current through said furnace body to heat said furnace body sufficient to atomize a sample on a platform within said furnace body, an elongated sample platform having a sample holding recess and being positioned centrally within said furnace body opposite said inlet aperture and integrally connected to said furnace body, web means for integrally connecting said platform to said furnace body, said web means being configured and positioned to maintain a substantially uniform electrical potential thereacross to substantially prevent a heat-generating current flow through said platform when current flows through said furnace body and to sufficiently impede heat conduction from said furnace body to said platform so that sample on said platform is thermally atomized substantially by radiation from said furnace body, said furnace body having a longitudinal axis and a longitudinal center plane containing said axis and extending through said inlet aperture, said web means comprising a single web extending between said furnace body and said platform and positioned in said center plane, said platform having a hollow, generally semicylindrical shape and disposed between said inlet aperture and said web and symmetrically arranged relative to said center plane, said web being constricted from said furnace body toward said platform to sufficiently impede heat conduction from said furnace body to said platform so that sample on said platform is thermally atomized substantially by radiation from said furnace body.

5. The device of claim 4 wherein said means for passing an electrical current comprises first and second electrical contacts disposed laterally on said furnace body so that electrical current flows in a circumferential direction through said furnace body and all positions on said web have substantially the same electrical potential.

6. An electrothermal atomization furnace comprising:

a tubular electrothermal furnace body adapted for passing a radiation beam therethrough, said furnace body having a centrally positioned lateral inlet pressure, means for passing an electrical current through said furnace body to heat said furnace body sufficient to atomize a sample on a platform within said furnace body, an elongated sample platform having a sample holding recess and being positioned centrally within said furnace body opposite said inlet aperture and integrally connected to said furnace body, web means for integrally connecting said platform to said furnace body, said web means being configured and positioned to maintain a substantially uniform electrical potential thereacross to substantially prevent a heat-generating current flow through said platform when current flows through said furnace body and to sufficiently impede heat conduction from said furnace body to said platform so that sample on said platform is thermally atomized substantially by radiation from said furnace body, said furnace body having a longitudinal axis and a longitudinal center plate containing said axis and extending through said inlet aperture, sad means for passing an electrical current comprises first and second electrical contacts, first and second generally semicylindrical hollow body members being oppositely disposed and extending around said furnace body to form a slot therebetween with said center plane extending through said slot, said first body member having a first web portion extending perpendicular to said center plane and connecting said first body member to said furnace body, said second body member having a second web portion extending perpendicular to said center plane and connecting said second body member to said furnace body, said first contact being integral with said first body member and having longitudinal axis extending perpendicular to said center plane, and said second contact being integral with said second body member and having a longitudinal axis extending perpendicular to said center plane.

7. An electrothermal atomization furnace comprising:

a tubular, electrically conductive furnace body having an interior wall and a central area, a sample-holding inner body integral with said furnace body, said inner body being spaced from said interior wall of said furnace body by an interconnecting integral web, said inner body being a hollow, generally semicylindrical shape and extending in an axial direction only through the central area of the furnace body, said furnace body has a lateral inlet port disposed at its central area and said semicylindrical inner body is arranged opposite said inlet port so as to be open towards said inlet port, and said inner body has a first side facing said inlet port and an opposite second side remote from said inlet port, said inner body being connected at it opposite side to said body by said web, said web extending in a circumferential direction along a portion of the circumference of said semicylindrical inner body.

8. The device of claim 7 wherein said web has a plurality of axial bores.

9. The device of claim 8 wherein said inner body has an inner surface with a plurality of projections forming a portion of a screw thread.

10. The device of claim 8 wherein said inner body has a smooth inner surface and oppositely disposed internally projecting collars to form a sample holding recess.

11. The device of claim 3 wherein said inner body has an inner surface with a plurality of projections forming a portion of a screw thread.

12. The device of claim 3 which comprises electrical contacts disposed laterally on said furnace body so that electrical current can be conducted in a circumferential direction through said furnace body.

13. An electrothermal atomization furnace comprising:
   a tubular, electrically conductive furnace body having an interior wall and a central area,
   a sample-holding inner body integral with said furnace body, said inner body being spaced from said interior wall of said furnace body by an interconnecting integral web,
   said inner body being a hollow, generally semicylindrical shape and extending in an axial direction only through the central area of the furnace body,
   first and second electrical contacts disposed laterally on said furnace body so that electrical current can be conducted in a circumferential direction through said furnace body,
   first and second generally semicylindrical hollow body members being oppositely disposed and extending around said furnace body to form a slot therebetween with a center plane of said furnace body extending through said slot, said first body member having a first web portion extending perpendicular to said center plane and connecting said first body member to said furnace body, said second body member having a second web portion extending perpendicular to said center plane and connecting said second body member to said furnace body,
   said first contact being integral with said first body member and having a longitudinal axis extending perpendicular to said center plane, and
   said second contact being integral with said second body member and having a longitudinal axis extending perpendicular to said center plane.

14. The device of claim 13 wherein said first and second web portions are constricted to increase electrical resistance and impede heat conduction therethrough.

15. A method of manufacturing a graphite atomizer furnace comprising
   forming an integral graphite tubular furnace body blank having a concentric, tubular inner body which is connected at its center by an annular web,
   axially boring said blank to reduce said inner body to a generally semicylindrical shape to form a sample-holding platform,
   axially boring said web to form a plurality of bores therein,
   milling said web to form annular recesses between said inner body and said outer body, and
   boring an inlet port through said furnace body opposite said semicylindrical inner body.

16. The method of claim 15 wherein the step of forming said furnace body blank comprises lathing a graphite workpiece.

17. The method of claim 16 further comprising threading the interior of the tubular inner body prior to axially boring said blank.

18. The method of claim 15 further comprises threading the interior of the tubular inner body prior to axially boring said blank.

19. The method of claim 15 wherein the step of axially boring said blank comprises boring a plurality of bores axially in said blank to remove approximately one-half of said inner body to form a semicylindrical inner body.

* * * * *